US009947091B2

(12) United States Patent
Govari et al.

(10) Patent No.: US 9,947,091 B2
(45) Date of Patent: Apr. 17, 2018

(54) LOCALLY APPLIED TRANSPARENCY FOR A CT IMAGE

(71) Applicant: Biosense Webster (Israel) Ltd., Yokneam (IL)

(72) Inventors: Assaf Govari, Haifa (IL); Vadim Gliner, Haifa (IL); Ram B. Mayer, Raanana (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 203 days.

(21) Appl. No.: 14/942,455

(22) Filed: Nov. 16, 2015

(65) Prior Publication Data

US 2017/0140527 A1    May 18, 2017

(51) Int. Cl.

| | |
|---|---|
| *G06K 9/00* | (2006.01) |
| *G06T 7/00* | (2017.01) |
| *G06T 15/00* | (2011.01) |
| *G06T 7/20* | (2017.01) |
| *G06K 9/46* | (2006.01) |
| *A61B 6/03* | (2006.01) |
| *A61B 8/13* | (2006.01) |
| *A61B 8/08* | (2006.01) |

(52) U.S. Cl.
CPC .......... *G06T 7/0012* (2013.01); *A61B 6/032* (2013.01); *A61B 6/037* (2013.01); *A61B 8/0841* (2013.01); *A61B 8/13* (2013.01); *G06K 9/00335* (2013.01); *G06K 9/4604* (2013.01); *G06T 7/004* (2013.01); *G06T 7/0085* (2013.01); *G06T 7/20* (2013.01); *G06T 15/00* (2013.01); *G06T 2200/04* (2013.01); *G06T 2207/10072* (2013.01); *G06T 2207/30004* (2013.01)

(58) Field of Classification Search
CPC ..... G06T 7/0012; G06T 7/004; G06T 7/0085; G06T 7/20; G06T 15/00; G06T 2200/04; G06T 2207/10072; G06T 2207/30004; G06K 9/00335; G06K 9/4604; A61B 6/032; A61B 6/037; A61B 8/084; A61B 8/13
See application file for complete search history.

(56) References Cited

U.S. PATENT DOCUMENTS 5,558,091 A * 9/1996 Acker ................... A61B 5/062
128/899
7,225,012 B1 * 5/2007 Susil ..................... A61B 90/36
600/407

(Continued)

OTHER PUBLICATIONS

European Search Report dated Apr. 24, 2017, Application No. EP 16 19 8933.

(Continued)

*Primary Examiner* — Shefali Goradia

(57) ABSTRACT

A method, including, receiving three-dimensional tomographic data with respect to a body of a living subject, and using the data to generate a representation of an external surface of the body and displaying the representation on a screen. The method further includes inserting an invasive instrument into a region of the body and identifying a position of the instrument in the body. The method also includes rendering an area of the external surface surrounding the identified position of the instrument locally transparent in the displayed representation, so as to make visible on the screen an internal structure of the body in a vicinity of the identified position.

28 Claims, 7 Drawing Sheets

(56) References Cited

U.S. PATENT DOCUMENTS

| | | | |
|---|---|---|---|
| 8,208,991 B2 * | 6/2012 | Markowitz | A61B 5/0422 600/424 |
| 9,398,936 B2 * | 7/2016 | Razzaque | A61B 8/4245 |
| 2003/0032878 A1 | 2/2003 | Shahidi | |
| 2007/0197896 A1 * | 8/2007 | Moll | A61B 1/00039 600/407 |
| 2012/0253200 A1 | 10/2012 | Stolka et al. | |

OTHER PUBLICATIONS

Christopher Bichlmeier, et al.: "Contextual Anatomic Mimesis Hybrid In-Situ Visualization Method for Improving Multi-Sensory Depth Perception in Medical Augmented Reality", Mixed and Augmented Reality, 2007. ISMAR 2007. 6$^{th}$ IEEE and ACM International Symposium on, IEEE, Piscataway, NJ, USA, Nov. 13, 2007 (Nov. 13, 2007), pp. 1-10, XP058089539, DOI: 10.1109/ISMAR. 2007.4538837, ISBN: 978-1-4244-1749-0.

Ramin Shahidi, et al.: "Implementation, Calibration and Accuracy Testing of an Image-Enhanced Endoscopy System", IEEE Transactions on Medical Imaging, IEEE Service Center, Picataway, NJ, US, vol. 21, No. 12, Dec. 2, 2002 (Dec. 2, 2002), XP011076403, ISSN: 0278-0062.

\* cited by examiner

… (1)

LOCALLY APPLIED TRANSPARENCY FOR A CT IMAGE

FIELD OF THE INVENTION

The present invention relates generally to image presentation, and specifically to image presentation for an invasive medical procedure.

BACKGROUND OF THE INVENTION

The advent of tomographic imaging systems, such as magnetic resonance imaging (MRI) and computerized tomography (CT) with X-rays, has enabled a physician performing an invasive procedure to visualize internal elements of a subject being operated on.

The tomographic imaging systems provide three-dimensional images to the physician, and are a significant improvement on the previously available simple X-ray systems. However, the images of a subject's internal structure generated from the tomographic data may in some cases provide too much visual information to the physician, so that limiting the visual information presented becomes useful.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides a method, including, receiving three-dimensional tomographic data with respect to a body of a living subject;

using the data to generate a representation of an external surface of the body and displaying the representation on a screen;

inserting an invasive instrument into a region of the body and identifying a position of the instrument in the body; and rendering an area of the external surface surrounding the identified position of the instrument locally transparent in the displayed representation, so as to make visible on the screen an internal structure of the body in a vicinity of the identified position.

Typically the tomographic data is derived from at least one of computerized tomography using X-rays, magnetic resonance imaging, positron emission tomography, single photon emission computed tomography, and ultrasound tomography.

In a disclosed embodiment the invasive instrument includes a sensor configured to generate a signal in response to a magnetic field traversing the sensor, and wherein identifying the position of the instrument includes using the signal to identify the position.

The method may include incorporating an icon representing the invasive instrument into the displayed representation. Additionally or alternatively, the method may include registering an imaging frame of reference of the representation with a tracking frame of reference used in tracking the position of the instrument.

In a further disclosed embodiment the method includes defining a bounding plane with respect to the identified position of the instrument, wherein the area of the external surface is on a first side of the bounding plane, and wherein the internal-structure-made-visible is on a second side, opposite the first side, of the bounding plane.

The method may include defining a bounding region, surrounding the identified position, within the bounding plane, so that the area of the external region and the internal-structure-made-visible, when projected orthogonally to the bounding plane, lie within the bounding region. Typically, the representation of the external surface includes a projection of the external onto an image plane, and wherein the bounding plane is parallel to the image plane. Alternatively, the representation of the external surface includes a projection of the external surface onto an image plane, and wherein the bounding plane is not parallel to the image plane.

The bounding plane may contain the identified position of the instrument. Alternatively, the bounding plane may not contain the identified position of the instrument.

The tomographic data may include computerized tomographic (CT) data derived from X-rays of the body of the living subject, and a region of the internal structure of the body having a low attenuation of the X-rays may be rendered transparent in the displayed representation.

In a yet further disclosed embodiment the internal structure in the displayed representation includes a non-segmented image derived from the tomographic data.

In an alternative embodiment the region of the body includes a nasal sinus of the living subject. The invasive instrument may be a guidewire inserted into the nasal sinus.

There is further provided, according to an embodiment of the present invention, apparatus, including:

an invasive instrument configured to be inserted into a region of a body of a living subject;

a screen configured to display a representation of an external surface of the body; and a processor configured to:

receive three-dimensional tomographic data with respect to the body, use the data to generate the representation of the external surface, identify a position of the instrument in the body, and render an area of the external surface surrounding the identified position of the instrument locally transparent in the displayed representation, so as to make visible on the screen an internal structure of the body in a vicinity of the identified position.

The present disclosure will be more fully understood from the following detailed description of the embodiments thereof, taken together with the drawings, in which:

DETAILED DESCRIPTION OF EMBODIMENTS

Overview

During an invasive medical procedure on the body of a living subject, especially a minimally invasive procedure, internal elements that are being operated on, or that are in the vicinity of such elements, are typically not visible to a physician performing the procedure. While an invasive instrument used in the procedure may be tracked, and overlaid on an image of the subject, such a composite image may be hard for the physician to interpret, typically since, inter alia, there may be relatively large amounts of visual information presented in the composite image.

Embodiments of the present invention provide a solution to this problem. Three-dimensional tomographic data of the body of the subject is received by a processor operating a system configured to identify a position of an invasive instrument used in the procedure. The tomographic data may be received some time, possibly even days, before the actual procedure is performed. The data is used to generate a representation of an external surface of the body, typically approximating to the skin of the subject, and the representation is displayed on a screen.

During the procedure a physician inserts an invasive instrument, such as a guidewire, into a region of the subject's body. The processor operates an instrument tracking system, such as a magnetic tracking system that tracks a magnetic sensor in the instrument, to identify a position of the instrument within the subject's body.

The processor delineates an area of the external surface surrounding the identified position, and renders the area locally transparent in the displayed representation of the surface. The area rendered locally transparent may be selected to be according to the position of a viewer of the external surface. Typically, the area is parallel to a screen on which the external surface is imaged, so that the screen acts as a "virtual camera" for the viewer. Rendering the area locally transparent makes visible on the screen internal structure of the body in the vicinity of the identified position. This internal structure was previously obscured by the external surface.

Typically, the dimensions of the area made locally transparent may be adjusted by the physician. Alternatively or additionally, the dimensions may be pre-set so that the processor at least partly delineates the area automatically.

By showing internal structure of the body, but limiting the area shown to a region surrounding the position of the invasive instrument, embodiments of the present invention provide useful information to the physician without generating a visual "overload."

System Description

Figure 1:
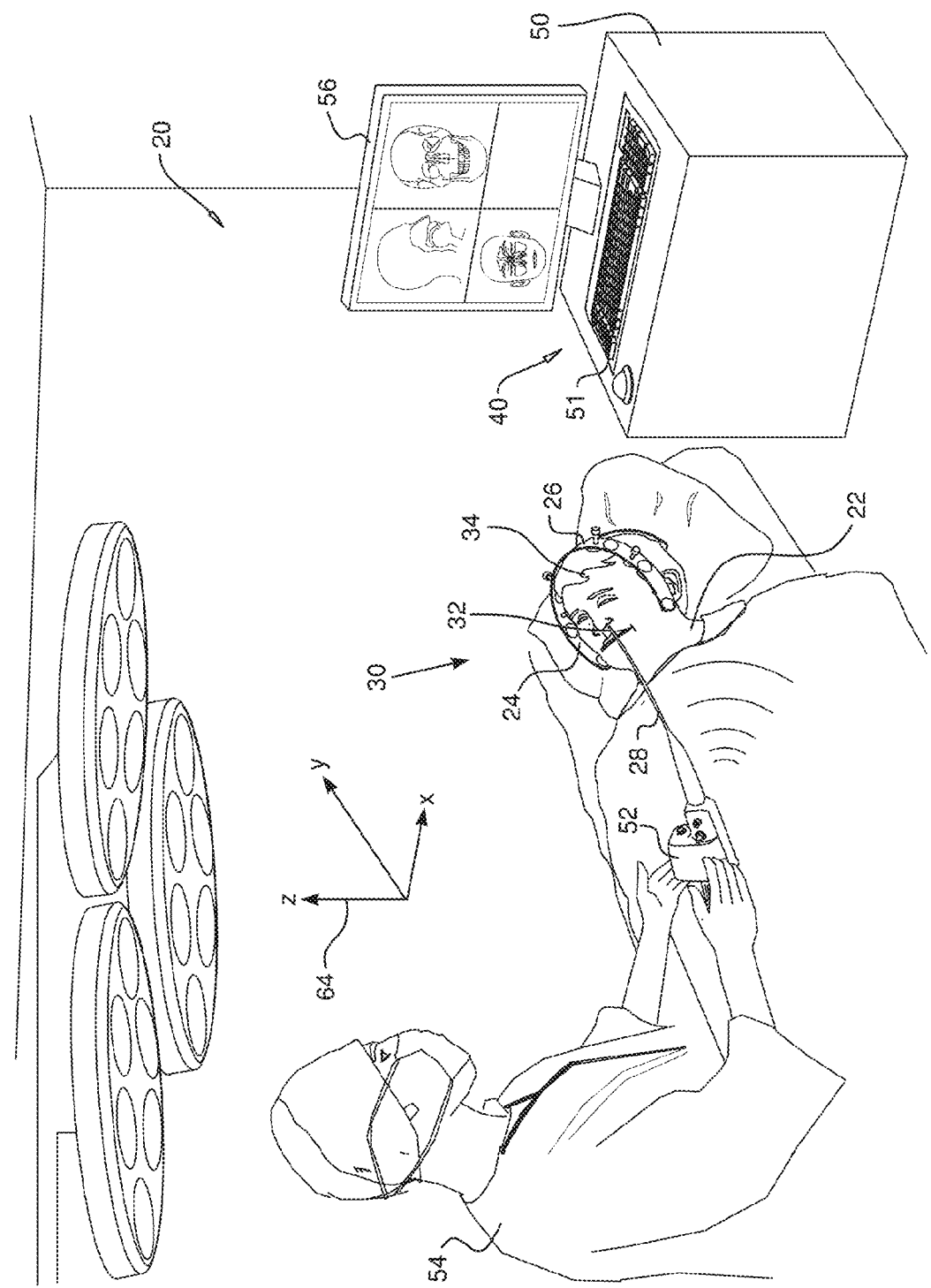
FIG. 1 is a schematic illustration of a nasal sinus surgery system, according to an embodiment of the present invention.
Figure 2:
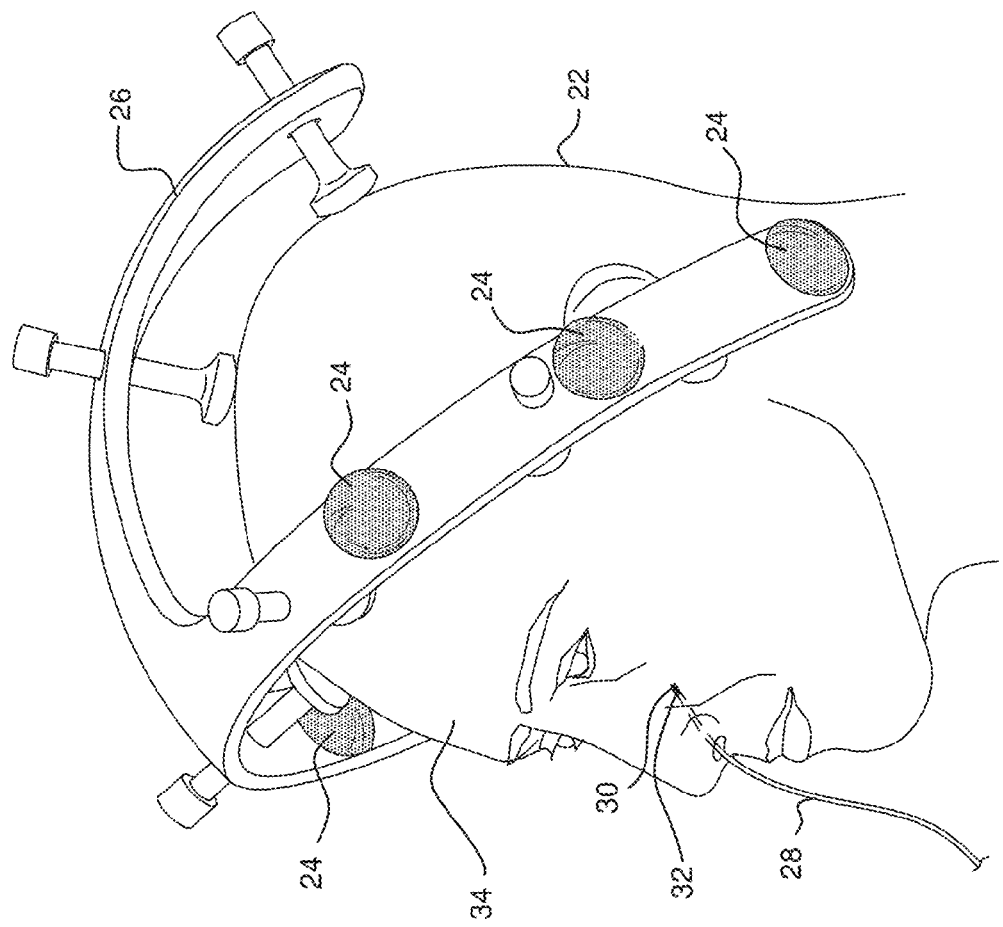
FIG. 2 is a schematic illustration of the head of a subject undergoing surgery with the system of FIG. 1, according to an embodiment of the present invention.

Reference is now made to FIG. 1, which is a schematic illustration of a nasal sinus surgery system 20, and to FIG. 2, which is a schematic illustration of the head of a subject 22 undergoing surgery with the system, according to an embodiment of the present invention. System 20 is typically used during a medical procedure on a nasal sinus of subject 22. Prior to such a procedure, a set of magnetic field generators 24 are fixed to the head of the subject, typically by incorporating the generators into a frame 26 which is clamped to the subject's head. As is explained below, the field generators enable the position of an instrument 28 that is inserted into the nasal sinus of the subject, assumed to have an external surface 34, to be tracked.

For clarity in the following description, except where otherwise indicated, instrument 28 is assumed to comprise a guidewire having a coil 30 in its distal end 32, the guidewire being inserted into the sinus prior to a sinuplasty procedure. Coil 30 acts as a tracking sensor, and a method of tracking using the coil is described further below. Alternatively another type of sensor, such as a Hall device, may be used in place of coil 30. A guidewire similar to guidewire 28 is described in U.S. patent application Ser. No. 14/792,823, assigned to the assignee of the present invention, which is incorporated herein by reference. However, those having ordinary skill in the art will be able to adapt the description, mutatis mutandis, for the case of instruments other than guidewires that are inserted and tracked.

Elements of system 20, including generators 24, may be controlled by a system processor 40, comprising a processing unit communicating with one or more memories. Processor 40 may be mounted in a console 50, which comprises operating controls 51 that typically include a keypad and/or a pointing device such as a mouse or trackball. Console 50 also connects to other elements of system 20, such as a proximal end 52 of guidewire 28. A physician 54 uses the operating controls to interact with the processor while performing the procedure, and the processor may present results produced by system 20 on a screen 56. Typically, different images derived from the results may be presented on screen 56. More details of images that may be presented are described further below.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate and calibrate magnetic generators 24. The generators are operated so as to transmit alternating magnetic fields of different frequencies into a region in proximity to frame 26. Prior to being placed on the subject, the generators in the frame may be calibrated by positioning a coil in the region in known locations and orientations relative to the frame. Signals are induced in the coil by the alternating magnetic fields, and the processor acquires and records the signals. (The Carto® system produced by Biosense Webster, of Diamond Bar, Calif., uses a system similar to that described herein for finding the location and orientation of a coil in a region irradiated by magnetic fields.) The processor then formulates a calibration relationship between the locations and orientations of the coil, and the recorded signals for these locations and orientations. It will be understood that processor 40 may track the location and orientation of coil 30, and thus of distal end 32 of guidewire 28, using the calibration relationship.

Once the calibration relationship has been formulated, the frame may be placed on the subject's head. After placement, the frame is fixed in position, and registered with external features of the subject's head, for example by imaging the subject's head with the attached frame from a number of different angles. The frame registration also registers the magnetic field generators with the subject's external features. Alternatively or additionally, the registration may include placing a coil in one or more known locations and orientations with respect to the external features of the subject as well as with the frame.

By registering with the subject's external features, the registration typically includes registration with the subject's sinuses using an image of the head which has usually been acquired prior to the projected sinuplasty procedure referred to above. Thus frame 26 is in registration with the subject's sinuses and with the subject's external features. The image used is formed from tomographic data received from the subject, and the tomographic data may be derived from tomographic procedures that include, but are not limited to, computerized tomography (CT) using X-rays, MRI (magnetic resonance imaging), positron emission tomography (PET), single photon emission computed tomography (SPECT) or ultrasound tomography. While, alternatively or additionally, the image may be comprised of a combination of such images, for simplicity in the following description the image is assumed to be derived from CT data, and those having ordinary skill in the art will be able to adapt the description for an image derived from other tomographic data.

The registration described above ensures that separate frames of reference, respectively defined by generators 24, features of the subject's head, and the CT image, are registered together, so that there is effectively one common frame of reference 64 that may be used in referring to elements derived from all three entities. By way of example, in the present description frame of reference 64 is assumed to be defined by the sagittal and coronal planes of subject 22, the intersection of the planes defining a direction of a y-axis, herein assumed to be upwards with respect to the subject, a direction of an x-axis being orthogonal to the y-axis, lying in the coronal plane, and towards the left of the subject, and a direction of a z-axis being orthogonal to the x and y axes and forwards from the subject.

The CT image referred to is derived from a set of voxels, each voxel comprising an ordered triple representing the position of the voxel in three-dimensional (3D) space such as may be defined by frame of reference 64. Each voxel also comprises a value representing a characteristic of the voxel, typically its attenuation to X-rays. The set of voxels is used to generate the CT image, typically by assigning different gray levels to the attenuation value of each of the voxels. As is known in the art, attenuation values are typically measured in Hounsfield units (HU), where air is −1000 HU corresponding to virtually no X-ray attenuation, and dense bone is approximately +3000 HU, corresponding to high X-ray attenuation. A typical gray level CT image used in a medical context presents voxels having values of −1000 HU as black, and those having values of +3000 as white.

Figure 3:
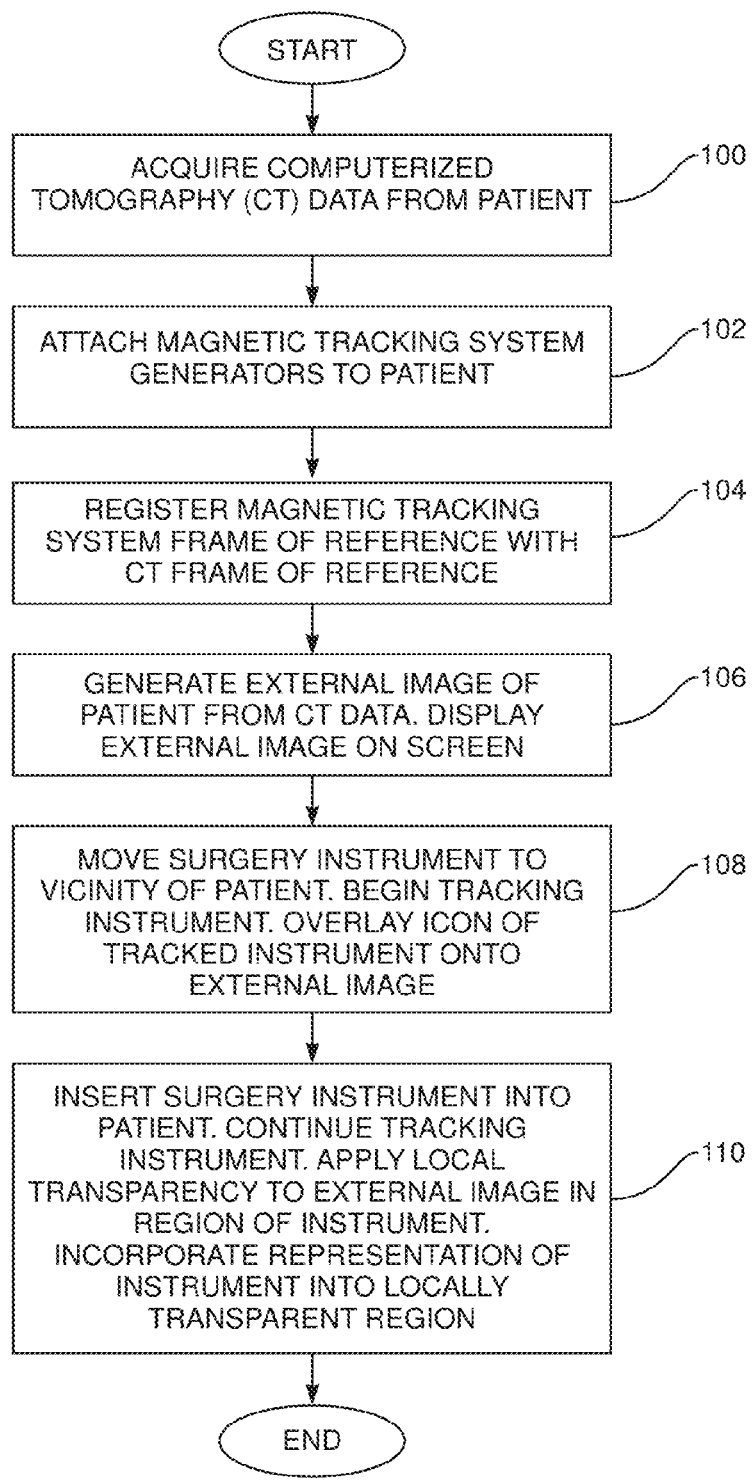
FIG. 3 is a flowchart of steps that are implemented in the operation of the system, according to an embodiment of the present invention.

FIG. 3 is a flowchart of steps that are implemented in the operation of system 20, and FIGS. 4-7 illustrate the steps, according to an embodiment of the present invention. The flowchart describes how an image of a sinus surgery procedure performed by physician 54 is presented on screen 56 to the physician.

In an initial step 100, the head of subject 22 is scanned by computerized tomography (CT), and the CT data from the scan is acquired by processor 40. The CT scan of subject 22 may be performed independently of the implementation of the remaining steps of the flowchart, which correspond to the sinus surgery procedure. Typically, step 100 may be performed a number of days before the following surgery steps of the procedure.

In a first surgical step 102, which is usually performed after subject 22 has been anaesthetized, magnetic generators 24 are fixedly mounted with respect to the head of subject 22, typically by clamping frame 26 to the subject's head. The generators are then operated, and in a registration step 104 a tracking frame of reference of the generators is registered with the frame of reference of the subject's head. The registration is typically as described above, i.e., by imaging the subject's head from different angles and/or by placing a coil in one or more known locations and orientations with respect to the external features of the subject as well as with the frame holding the generators. The registration produces a common frame of reference, herein assumed to comprise frame of reference 64.

Figure 4:
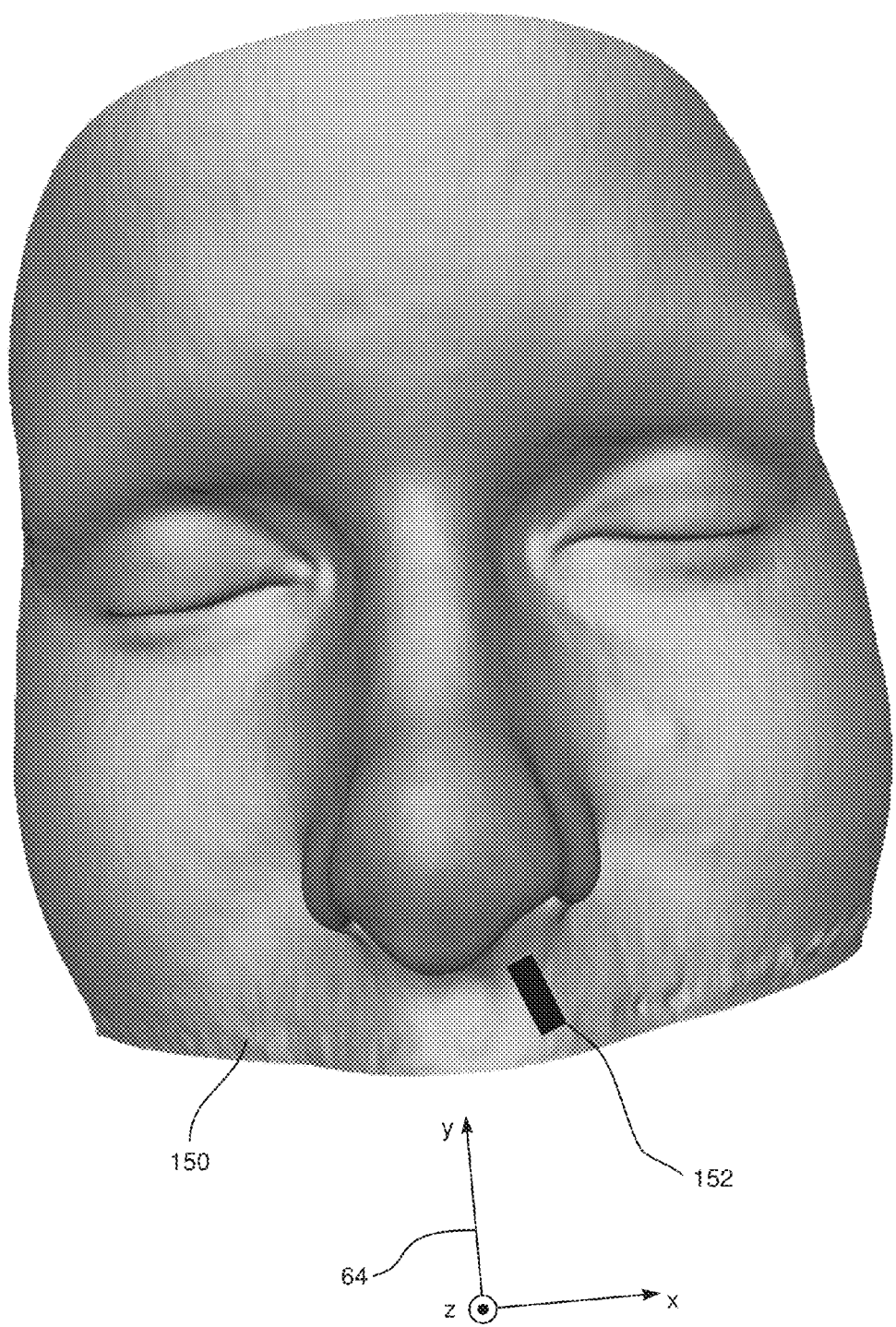
FIG. 4 schematically illustrates an image as displayed on a screen of the system, according to an embodiment of the present invention.

In an initial display step 106, processor 40 generates a representation 150, also referred to herein as image 150, of external surface 34 of the subject, using the CT data received in step 100, and displays the image on screen 56. FIG. 4 schematically illustrates image 150 as displayed on screen 56. Image 150 is assumed to be formed on a plane parallel to the coronal plane of the subject, i.e., parallel to an xy plane of frame of reference 64, the axes of which are also drawn in FIG. 4.

In an instrument operation step 108, the physician brings instrument 28 into proximity with the sinuses of the subject, for example by positioning a distal tip of the instrument close to a nostril of the subject. Coil 30, in response to the magnetic field from generators 24, provides a signal to processor 40 which enables the processor to determine a position and an orientation of the coil, and thus of distal tip 32 of guidewire 28. The processor uses the position and orientation of the distal tip to overlay an icon 152, having a position and orientation representative of those of the distal tip, onto image 150, as illustrated in FIG. 4.

In some embodiments, physician 54 may visually verify the registration of step 104 at this stage, and if necessary make adjustments to the registration using controls 51. The verification may be made by the physician observing the placement of distal tip 32 with respect to the subject's nostril, and confirming that the representation of icon 152 with respect to image 150 appears to be correct. If the representation does not appear to be correct, the physician may use controls 51 to manually adjust icon 152 with respect to image 150, and processor 40 may incorporate the adjustment made into the registration of the frames of reference of generators 24 with image 150.

In an invasive step 110, the physician inserts instrument 28 into the nostril of the subject, so that the instrument distal tip is no longer visible to the physician. Processor 40 continues tracking the distal tip, and moves icon 152 so that the tracked position and orientation of the distal tip is represented by the position and orientation of the icon in image 150.

In some embodiments a representation of instrument 28 is also incorporated into image 150. If instrument 28 is rigid, then the representation may be derived from a geometric relationship of coil 30 with the instrument, by methods which are known in the art. If instrument 28 is flexible, then the representation may be generated using further tracking coils, generally similar to coil 30, installed into the instrument. Alternatively, the position of coil 30 may be recorded, and the representation of the instrument may be assumed to correspond to the recorded track.

Figure 5:
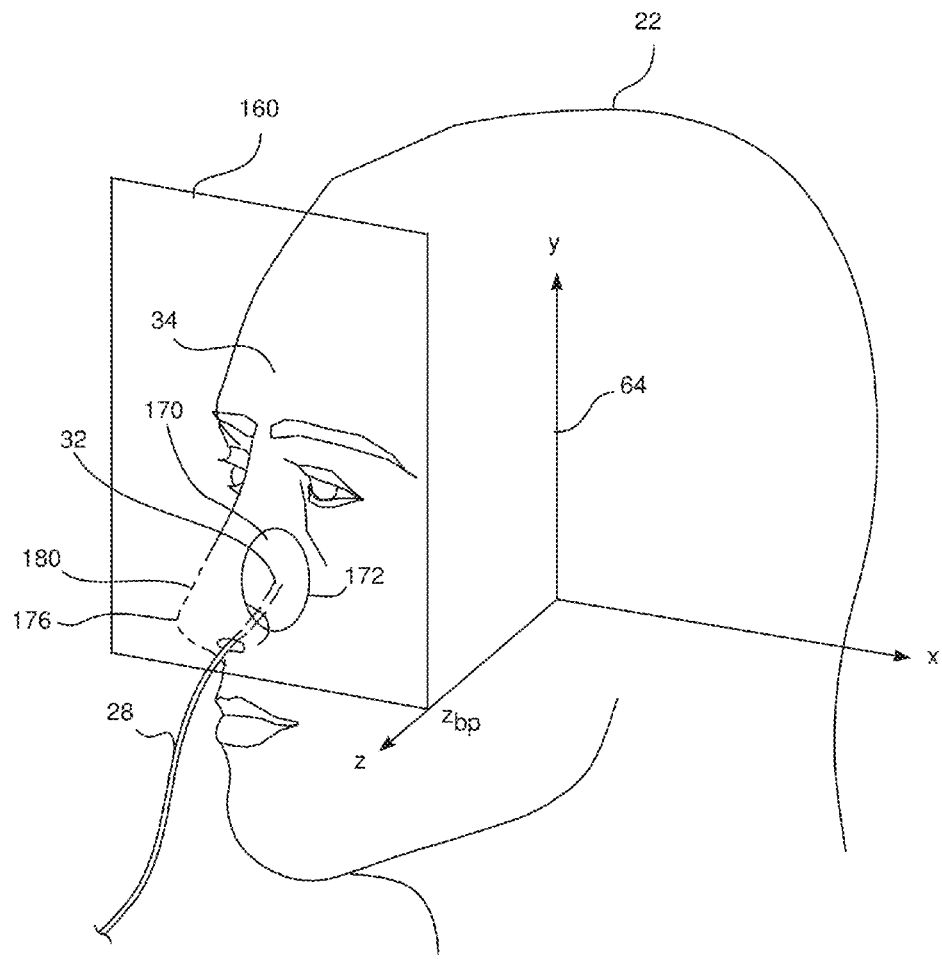
FIG. 5 schematically illustrates a boundary plane and a bounding region; according to an embodiment of the present invention.

FIG. 5 schematically illustrates a boundary plane 160 and a bounding region 170. The position of distal tip 32 is used to delineate regions of image 150 which are to be rendered transparent, and those which are to be left "as is." In order to perform the delineation, the position of the distal tip is used to define boundary plane 160, and bounding region 170 surrounding the distal tip and in the boundary plane. As described below, processor 40 uses the boundary plane and the bounding region to determine which elements of image 150 are to be rendered locally transparent, and which elements are to be not so rendered.

In one embodiment boundary plane 160 is a plane which passes through the position of distal tip 32, and the direction of the boundary plane may be set automatically by processor 40. Alternatively or additionally, the direction and/or the position of the boundary plane may be set by physician 54 using controls 51. For clarity, the following description assumes that the boundary plane and the position of the distal tip are defined according to frame of reference 64, which is assumed to have its origin in subject 22. The distal tip is assumed to have a positive z value of $z_{bp}$, and, by way of example, boundary plane 160 is assumed to be parallel to an xy plane of frame of reference 64, i.e., is parallel to the coronal plane of the subject, and to pass through the position of the distal tip, as is illustrated schematically in FIG. 5. Since boundary plane 160 passes through the position of the distal tip, an equation for the boundary plane is:

$$z=z_{bp} \qquad (1)$$

Bounding region 170 may also be set automatically by processor 40, and/or at least partly manually by physician 54. Bounding region 170 may be any closed area in the bounding plane that has a perimeter 172 and that surrounds the position of distal tip 32. For simplicity, in the following description area 170 is assumed to be circular, having its center at the position of the distal tip and its radius set by physician 54, but those having ordinary skill in the art will be able to adapt the description for any regular or irregular closed area surrounding the position of the distal tip.

Processor 40 determines elements of image 150 having values of $z \geq z_{bp}$, and that, when projected along the z-axis, lie within area 170. The processor then renders the elements transparent so that, consequently, these elements are no longer visible in image 150. For example, in FIG. 5 a tip 176 of the nose of subject 22 has a value $z \geq z_{bp}$, so a broken line 180 in the vicinity of the subject's nose tip illustrates parts of external surface 34 that are no longer visible in image 150.

In consequence of the above-defined elements being rendered transparent, elements of image 150, having values of $z<z_{bp}$ and that when projected along the z-axis lie within area 170 are now visible, so are displayed in the image. Prior to the locally transparent rendering, the "now visible" elements were not visible since they were obscured by surface elements.

Figure 6:
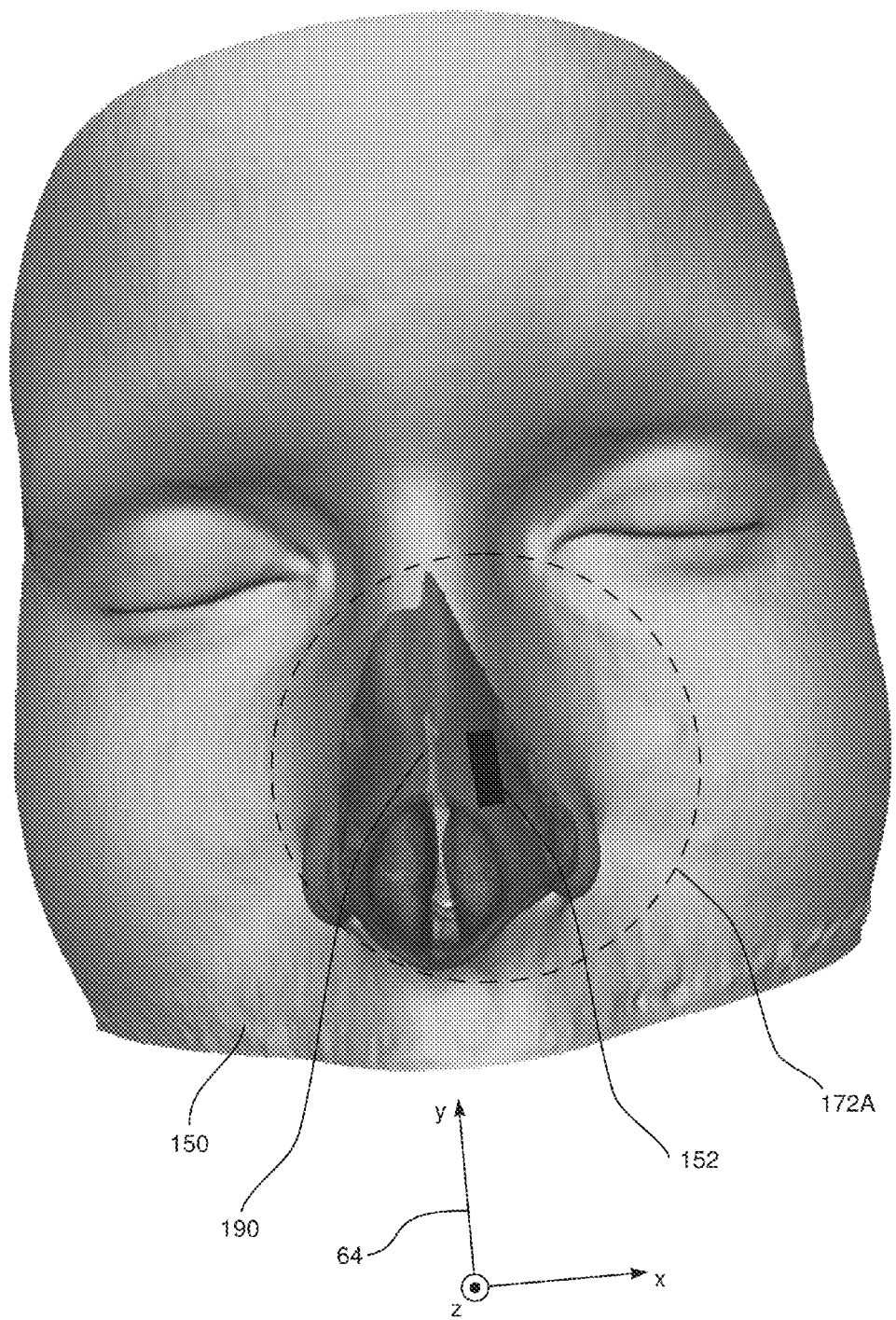
FIG. 6 schematically illustrates the image displayed on the screen after local transparency rendering of elements of the image; according to an embodiment of the present invention.

FIG. 6 schematically illustrates image 150 as displayed on screen 56 after the local transparency rendering of the elements of the image within area 170. For clarity a broken circle 172A, corresponding to perimeter 172 (FIG. 5) has been overlaid on the image, and frame of reference 64 is also drawn in the figure. Because of the transparent rendering of elements within circle 172A, an area 190 within the circle now shows internal structure, derived from the CT tomographic data received in step 100, of subject 22.

It will be appreciated that in the case illustrated in FIG. 6 screen 56 is in an xy plane, so that the screen acts as a "virtual camera" of a viewer looking towards image 150 along a z axis.

The description above provides one example of the application of local transparency to an image derived from tomographic data, the image in this case being formed on a plane parallel to the coronal plane of the subject. It will be understood that because of the three-dimensional nature of the tomographic data, the data may be manipulated so that embodiments of the present invention may use images formed on substantially any plane through subject 22, and that may be defined in frame of reference 64.

Figure 7:
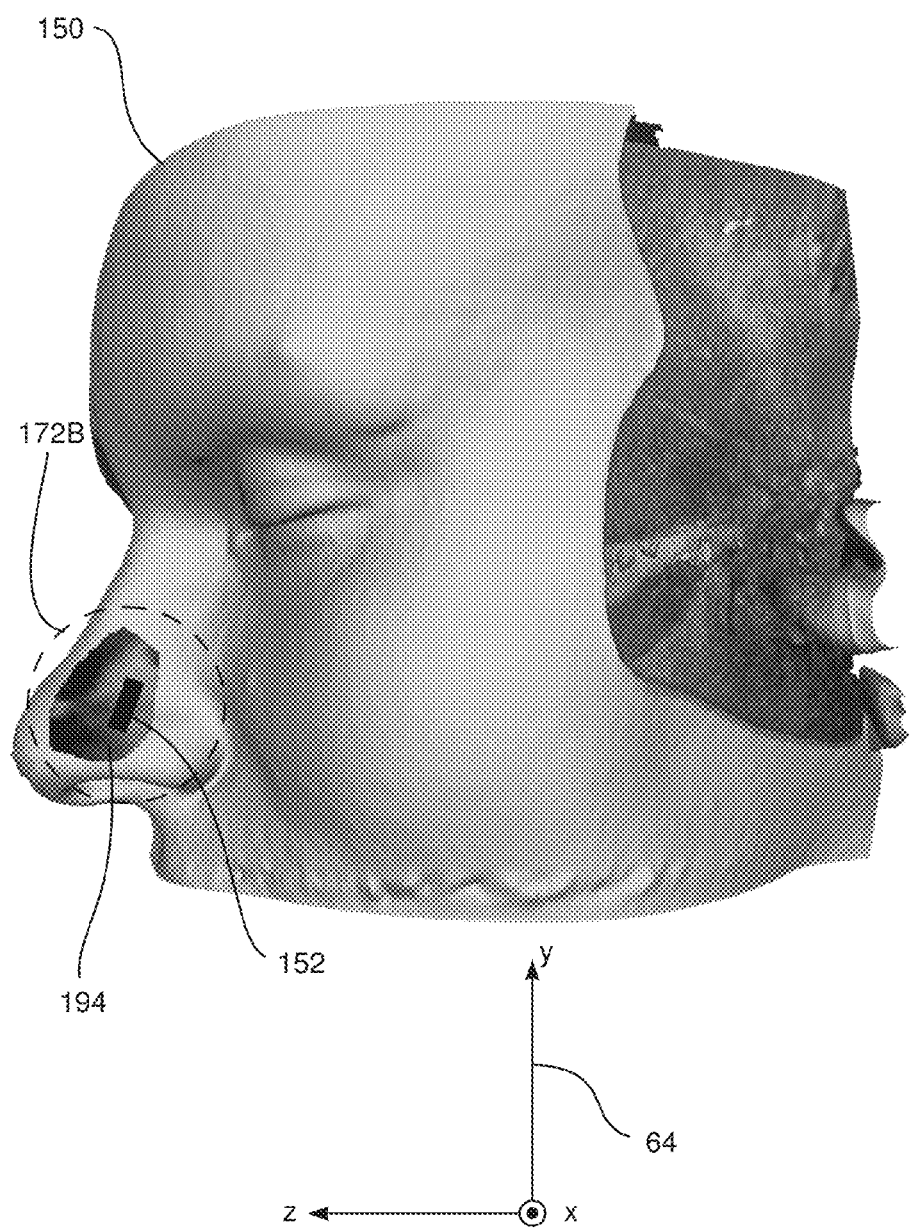
FIG. 7 schematically illustrates the image displayed on the screen, according to an alternative embodiment of the present invention.

FIG. 7 schematically illustrates image 150 as displayed on screen 56, according to an alternative embodiment of the present invention. In FIG. 7, image 150 is assumed to be formed using a bounding plane parallel to the sagittal plane of subject 22, i.e. on a yz plane of frame of reference 64. The location of the yz plane is assumed to correspond to the x value of distal tip 32, herein termed $x_{bp}$, so that an equation of the bounding plane is given by equation (2):

$$x=x_{bp} \qquad (2)$$

As for the example described above with reference to FIGS. 5 and 6, a bounding region surrounding the distal tip and lying on the bounding plane is assumed to be, for simplicity and by way of example, circular with a center at the position of distal tip 32 and a radius that is set by physician 54. In FIG. 7, a broken circle 172B, centered on icon 152 corresponds to the perimeter of the bounding region.

For the embodiment illustrated in FIG. 7, processor 40 determines elements of image 150 having values of $x \geq x_{bp}$, that, when projected along the x-axis, lie within the bounding region. The processor then renders these elements transparent so that they are no longer visible in image 150. As a consequence of the rendered local transparency, elements 194 of image 150, within circle 172B, having values of $x<x_{bp}$ and that when projected along the x-axis lie within the bounding region, are now visible in image 150.

In FIG. 7, in contrast to FIG. 6, screen 56 is now in a yz plane, and the screen acts as a virtual camera of a viewer looking towards image 150 along an x axis.

It will be understood that in general, for any given bounding plane and bounding region, the processor determines elements of image 150 that are above the plane and that, when projected orthogonally onto the bounding plane, lie within the bounding region. The processor renders these elements transparent, so that elements that are below the plane and that project orthogonally onto the bounding plane become visible in image 150.

It will also be understood that FIGS. 6 and 7 illustrate but two examples of embodiments of the present invention, and other embodiments will be apparent to those having ordinary skill in the art. Some examples are presented below.

Rather than the position of the instrument distal tip lying on the bounding plane referred to above, the plane may be above or below the distal tip. In some embodiments the distance between the plane and the distal tip may be varied by physician 54, typically during a procedure being performed by the physician, so enabling the physician to view images, other than those exemplified above, of desired internal structures of subject 22.

The dimensions of the bounding region may be varied to enable the physician to also view other desired images of internal structures.

The physician may vary the direction of the bounding plane, for example to enhance the visibility of particular internal structures. While the bounding plane is typically parallel to the plane of the image presented on screen 56, this is not a requirement, so that if, for example, the physician wants to see more detail of a particular structure, she/he may rotate the bounding plane so that it is no longer parallel to the image plane.

In the case of CT images, the internal structures of subject 22 that are made visible by the application of local transparency, as described above, are based on CT voxel data having measured attenuation values. While the internal structure images are typically generated with the low attenuation voxels, such as those for air, being represented by black or white opaque pixels on screen 56, in some embodiments of the present invention the pixels of the low attenuation voxels of the internal structures are rendered transparent. Rendering transparent the pixels corresponding to low attenuation voxels makes internal structure obscured by these voxels visible. Thus, since the low attenuation voxels typically correspond to air, which is transparent to visible light, making visible the structure normally obscured by the voxels provides a more realistic display for image 150.

Some displays of tomographic data use segmentation in order to make images generated more meaningful. However, the inventors have observed that such segmentation may generate confusing, or even incorrect, images. Thus, in some embodiments of the present invention, non-segmented, "raw" images derived from the tomographic data, including images of the subject's external surface and internal structure, are displayed on screen 56, rather than segmented images.

While the description above refers to one distal tip of a guidewire and an associated locally transparent region, those having ordinary skill in the art will be able to adapt the description to cover cases of tools other than guidewires, as well as cases where multiple tools are tracked simultaneously, each of the tools having a respective locally transparent region.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising,
receiving three-dimensional tomographic data with respect to a body of a living subject;
using the data to generate a representation of an external surface of the body and displaying the representation on a screen;
inserting an invasive instrument into a region of the body and identifying a position of the instrument in the body;
rendering an area of the external surface surrounding the identified position of the instrument locally transparent in the displayed representation, so as to make visible on the screen an internal structure of the body in a vicinity of the identified position; and
defining a bounding plane with respect to the identified position of the instrument, wherein the area of the external surface is on a first side of the bounding plane, and wherein the internal-structure-made-visible is on a second side, opposite the first side, of the bounding plane.

2. The method according to claim 1, wherein the tomographic data is derived from at least one of computerized tomography using X-rays, magnetic resonance imaging, positron emission tomography, single photon emission computed tomography, and ultrasound tomography.

3. The method according to claim 1, wherein the invasive instrument comprises a sensor configured to generate a signal in response to a magnetic field traversing the sensor, and wherein identifying the position of the instrument comprises using the signal to identify the position.

4. The method according to claim 1, and comprising incorporating an icon representing the invasive instrument into the displayed representation.

5. The method according to claim 1, and comprising registering an imaging frame of reference of the representation with a tracking frame of reference used in tracking the position of the instrument.

6. The method according to claim 1, and comprising defining a bounding region, surrounding the identified position, within the bounding plane, so that the area of the external region and the internal-structure-made-visible, when projected orthogonally to the bounding plane, lie within the bounding region.

7. The method according to claim 1, wherein the representation of the external surface comprises a projection of the external onto an image plane, and wherein the bounding plane is parallel to the image plane.

8. The method according to claim 1, wherein the representation of the external surface comprises a projection of the external surface onto an image plane, and wherein the bounding plane is not parallel to the image plane.

9. The method according to claim 1, wherein the bounding plane contains the identified position of the instrument.

10. The method according to claim 1, wherein the bounding plane does not contain the identified position of the instrument.

11. The method according to claim 1, wherein the tomographic data comprises computerized tomography (CT) data derived from X-rays of the body of the living subject, and wherein a region of the internal structure of the body having a low attenuation of the X-rays is rendered transparent in the displayed representation.

12. The method according to claim 1, wherein the internal structure in the displayed representation comprises a non-segmented image derived from the tomographic data.

13. The method according to claim 1, wherein the region of the body comprises a nasal sinus of the living subject.

14. The method according to claim 13, wherein the invasive instrument comprises a guidewire inserted into the nasal sinus.

15. Apparatus, comprising:
an invasive instrument configured to be inserted into a region of a body of a living subject;
a screen configured to display a representation of an external surface of the body; and
a processor configured to:
receive three-dimensional tomographic data with respect to the body,
use the data to generate the representation of the external surface,
identify a position of the instrument in the body,
render an area of the external surface surrounding the identified position of the instrument locally transparent in the displayed representation, so as to make visible on the screen an internal structure of the body in a vicinity of the identified position, and
define a bounding plane with respect to the identified position of the instrument, wherein the area of the external surface is on a first side of the bounding plane, and wherein the internal-structure-made-visible is on a second side, opposite the first side, of the bounding plane.

16. The apparatus according to claim 15, wherein the tomographic data is derived from at least one of computerized tomography using X-rays, magnetic resonance imaging, positron emission tomography, single photon emission computed tomography, and ultrasound tomography.

17. The apparatus according to claim 15, wherein the invasive instrument comprises a sensor configured to generate a signal in response to a magnetic field traversing the sensor, and wherein identifying the position of the instrument comprises using the signal to identify the position.

18. The apparatus according to claim 15, wherein the processor is configured to incorporate an icon representing the invasive instrument into the displayed representation.

19. The apparatus according to claim 15, wherein the processor is configured to register an imaging frame of reference of the representation with a tracking frame of reference used in tracking the position of the instrument.

20. The apparatus according to claim 15, wherein the processor is configured to define a bounding region, surrounding the identified position, within the bounding plane, so that the area of the external region and the internal-structure-made-visible, when projected orthogonally to the bounding plane, lie within the bounding region.

21. The apparatus according to claim 15, wherein the representation of the external surface comprises a projection of the external surface onto an image plane, and wherein the bounding plane is parallel to the image plane.

22. The apparatus according to claim 15, wherein the representation of the external surface comprises a projection of the external surface onto an image plane, and wherein the bounding plane is not parallel to the image plane.

23. The apparatus according to claim 15, wherein the bounding plane contains the identified position of the instrument.

24. The apparatus according to claim 15, wherein the bounding plane does not contain the identified position of the instrument.

25. The apparatus according to claim 15, wherein the tomographic data comprises computerized tomographic (CT) data derived from X-rays of the body of the living subject, and wherein a region of the internal structure of the body having a low attenuation of the X-rays is rendered transparent in the displayed representation.

26. The apparatus according to claim 15, wherein the internal structure in the displayed representation comprises a non-segmented image derived from the tomographic data.

27. The apparatus according to claim 15, wherein the region of the body comprises a nasal sinus of the living subject.

28. The apparatus according to claim 27, wherein the invasive instrument comprises a guidewire inserted into the nasal sinus.

* * * * *